(12) United States Patent
Myoung et al.

(10) Patent No.: US 11,185,494 B2
(45) Date of Patent: Nov. 30, 2021

(54) SKIN WHITENING COMPOSITION COMPRISING CULTURE OF PSEUDOALTEROMONAS CARRAGEENOVORA OR EXTRACT THEREOF

(71) Applicant: Amorepacific Corporation, Seoul (KR)

(72) Inventors: Kilsun Myoung, Yongin-si (KR); Jaeyoung Ko, Yongin-si (KR); Yong Jin Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 16/647,352

(22) PCT Filed: Sep. 20, 2018

(86) PCT No.: PCT/KR2018/011114
§ 371 (c)(1),
(2) Date: Mar. 13, 2020

(87) PCT Pub. No.: WO2019/066376
PCT Pub. Date: Apr. 4, 2019

(65) Prior Publication Data
US 2020/0315951 A1 Oct. 8, 2020

(30) Foreign Application Priority Data

Sep. 27, 2017 (KR) ........................ 10-2017-0125339

(51) Int. Cl.
| | | |
|---|---|---|
| *A61K 36/05* | (2006.01) | |
| *A61K 8/99* | (2017.01) | |
| *A61Q 19/02* | (2006.01) | |
| *C12N 1/20* | (2006.01) | |

(52) U.S. Cl.
CPC ............... *A61K 8/99* (2013.01); *A61Q 19/02* (2013.01); *C12N 1/20* (2013.01); *A61K 2800/40* (2013.01)

(58) Field of Classification Search
None
See application file for complete search history.

(56) References Cited

U.S. PATENT DOCUMENTS

| | | | |
|---|---|---|---|
| 7,022,668 B2 | 4/2006 | Parente Duena et al. | |
| 8,420,355 B2 | 4/2013 | Joncour Genicot et al. | |
| 2011/0195103 A1* | 8/2011 | Perez Arcas | A61P 17/02 424/401 |
| 2017/0333491 A1 | 11/2017 | Soley Astals et al. | |

FOREIGN PATENT DOCUMENTS

| | | |
|---|---|---|
| CN | 105950590 B | 7/2019 |
| JP | 4252444 B2 | 4/2009 |
| KR | 10-0784486 B1 | 12/2007 |
| KR | 10-0812922 B1 | 3/2008 |
| KR | 10-2010-0109743 A | 10/2010 |
| KR | 10-2012-0068367 A | 6/2012 |
| KR | 10-2014-0024840 A | 3/2014 |
| KR | 10-2016-0126204 A | 11/2016 |
| KR | 10-2016-0146112 A | 12/2016 |
| KR | 10-1686399 B1 | 12/2016 |
| KR | 10-2017-0072341 A | 6/2017 |
| WO | 2008/084890 A1 | 7/2008 |
| WO | 2009/106343 A1 | 9/2009 |
| WO | 2012/072245 A2 | 6/2012 |
| WO | 2016/001551 A1 | 1/2016 |

OTHER PUBLICATIONS

Blast2 alignment of SEQ ID No. 1 and the 16S rRNA sequence of Pseudoalteromonas strain No. J021 of Tebben et al., NCBI web site, https://blast.ncbi.nlm.nih.gov/Blast.cgi?PAGE=MegaBlast&PROGRAM=blastn&BLAST_PROGRAMS=megaBlast&PAGE_TYPE=BlastSearch&BLAST_SPEC=blast2seq&DATABASE=n/a&QUERY=&SUBJECTS=, Apr. 19, 2021. (4 pages total).
Jan Tebben, et al., "Induction of Larval Metamorphosis of the Coral Acropora millepora by Tetrabromopyrrole Isolated from a Pseudoalteromonas Bacterium", PLoS ONE, Apr. 2011, pp. 1-8, vol. 6, No. 4.
John P. Bowman, "Bioactive Compound Synthetic Capacity and Ecological Significance of Marine Bacterial Genus *Pseudoalteromonas*", Marine Drugs, 2007, pp. 220-241, vol. 5.
Kasthuri Venkateswaran, et al., "Pseudoalteromonas peptidolytica sp. nov., a novel marine mussel-thread-degrading bacterium isolated from the Sea of Japan", International Journal of Systematic and Evolutionary Microbiology, 2000, pp. 565-574, vol. 50.
GenBank: AB680359.1: Pseudoalteromonas carrageenovora gene for 16S rRNA, partial sequence, strain: NBRC 12985 (Jan. 28, 2012).
Won-Jae Chi, et al., "Isolation and Characterization of an Agar-hydrolyzing Marine Bacterium, Pseudoalteromonas sp. H9, from the Coastal Seawater of the West Sea, South Korea", Microbiology and Biotechnology Letters, 2015, pp. 134-141, vol. 43, No. 2.
International Search Report of PCT/KR2018/011114 dated Dec. 27, 2018 [PCT/ISA/210].

* cited by examiner

*Primary Examiner* — Russell G Fiebig
(74) *Attorney, Agent, or Firm* — Sughrue Mion, PLLC

(57) ABSTRACT

Disclosed in the specification is a skin whitening composition comprising as an effective ingredient a *Pseudoalteromonas carrageenovora* strain, a lysate thereof, a culture thereof, or an extract from the strain, lysate, or culture. Also, the specification discloses a *Pseudoalteromonas carrageenovora* SNC 121 strain, deposited with accession number KCCM12049P, which exhibits a skin whitening function.

8 Claims, 4 Drawing Sheets
Specification includes a Sequence Listing.

[FIG. 1]

AGCGGTAACAGAAAGTAGCTTGCTACTTTGCTGACGAGCGGCGGACGGGTGAGTAATGCT
TGGGAACATGCCTTGAGGTGGGGGACAACAGTTGGAAACGACTGCTAATACCGCATAATG
TCTACGGACCAAAGGGGGCTTCGGCTCTCGCCTTTAGATTGGCCCAAGTGGGATTAGCTA
GTTGGTGAGGTAATGGCTCACCAAGGCAACGATCCCTAGCTGGTTTGAGAGGATGATCAG
CCACACTGGAACTGAGACACGGTCCAGACTCCTACGGGAGGCAGCAGTGGGGAATATTGC
ACAATGGGCGCAAGCCTGATGCAGCCATGCCGCGTGTGTGAAGAAGGCCTTCGGGTTGTA
AAGCACTTTCAGTCAGGAGGAAAGGTTAGTAGTTAATACCTGCTAGCTGTGACGTTACTG
ACAGAAGAAGCACCGGCTAACTCCGTGCCAGCAGCCGCGGTAATACGGAGGGTGCGAGCG
TTAATCGGAATTACTGGGCGTAAAGCGTACGCAGGCGGTTTGTTAAGCGAGATGTGAAAG
CCCCGGGCTCAACCTGGGAACTGCATTTCGAACTGGCAAACTAGAGTGTGATAGAGGGTG
GTAGAATTTCAGGTGTAGCGGTGAAATGCGTAGAGATCTGAAGGAATACCGATGGCGAAG
GCAGCCACCTGGGTCAACACTGACGCTCATGTACGAAAGCGTGGGGAGCAAACAGGATTA
GATACCCTGGTAGTCCACGCCGTAAACGATGTCTACTAGAAGCTCGGAACCTCGGTTCTG
TTTTTCAAAGCTAACGCATTAAGTAGACCGCCTGGGGAGTACGGCCGCAAGGTTAAAACT
CAAATGAATTGACGGGGGCCCGCACAAGCGGTGGAGCATGTGGTTTAATTCGATGCAACG
CGAAGAACCTTACCTACACTTGACATACAGAGAACTTACCAGAGATGGTTTGGTGCCTTC
GGGAACTCTGATACAGGTGCTGCATGGCTGTCGTCAGCTCGTGTTGTGAGATGTTGGGTT
AAGTCCCGCAACGAGCGCAACCCCTATCCTTAGTTGCTAGCAGGTAATGCTGAGAACTCT
AAGGAGACTGCCGGTGATAAACCGGAGGAAGGTGGGGACGACGTCAAGTCATCATGGCCC
TTACGTGTAGGGCTACACACGTGCTACAATGGCGCATACAGAGTGCTGCGAACTCGCGAG
AGTAAGCGAATCACTTAAAGTGCGTCGTAGTCCGGATTGGAGTCTGCAACTCGACTCCAT
GAAGTCGGAATCGCTAGTAATCGCGTATCAGAATGACGCGGTGAATACGTTCCCGGGCCT
TGTACACACCGCCCGTCACACCATGGGAGTGGGTTGCTCCAGAAGTAGATAGTCTAACCC
TCGGGAGGACG (SEQ ID NO: 1)

[FIG. 2]

Pseudoalteromonas carrageenovora cgIA gene for lambda-carrageenase, type strain ATCC 43555T
Sequence ID: AM397269.1  Length: 3300  Number of Matches: 1

Range 1: 131 to 740 GenBank Graphics                                    ▼ Next Match  ▲ Previous Match

| Score | Expect | Identities | Gaps | Strand |
|---|---|---|---|---|
| 1094 bits(592) | 0.0 | 605/611(99%) | 2/611(0%) | Plus/Plus |

```
Query   1    TTTTAAAAAGCATAAACTCAATATTTAGGAAATAGGTACAATCTAATTCCTCAACACGTT   60
             ||||||||||||||||||||||||||||||||||||||||||||||||||||||||||||
Sbjct   131  TTTTAAAAAGCATAAACTCAATATTTAGGAAATAGGTACAATCTAATTCCTCAACACGTT   190

Query   61   ATAAATAACTTAATGTAAGGAATGTTATGAAAATAAAAATTCTATCTGCAATGGTAGCTA   120
             ||||||||||||||||||||||||||||||||||||||||||||||||||||||||||||
Sbjct   191  ATAAATAACTTAATGTAAGGAATGTTATGAAAATAAAAATTCTATCTGCAATGGTAGCTA   250

Query   121  GCTCGTTATTAATTGGCTGCGTTATCCCTACCGTTAAAGCTTCTCAATCGGCTATTAAAA   180
             ||||||||||||||||||||||||||||||||||||||||||||||||||||||||||||
Sbjct   251  GCTCGTTATTAATTGGCTGCGTTATCCCTACCGTTAAAGCTTCTCAATCGGCTATTAAAA   310

Query   181  GTATTGAAACAAACCGAACAATTACTAAAGTTAGAACAGGAATGTTGAGTGGAGGCTCAT   240
             ||||||||||||||||||||||||||||||||||||||||||||||||||||||||||||
Sbjct   311  GTATTGAAACAAACCGAACAATTACTAAAGTTAGAACAGGAATGTTGAGTGGAGGCTCAT   370

Query   241  CAATCA-AACTTACAAGCTATGAAGGGACTGTAGCTGCATATAAGTTTAATGGAGAAAAA   299
             ||||||  ||| ||||||||||||||||||||||||||||||||||||||||||||||||
Sbjct   371  CAATCATAAC-TACAAGCTATGAAGGGACTGTAGCTGCATATAAGTTTAATGGAGAAAAA   429

Query   300  CTGTGGGAAAATGAACTCTCGGGTTTTAGGAATCATGATATTTGGGTTCAAGATATTAAT   359
             |||||||||||||||||||||||||||| |||||||||||||||||||||||||||||||
Sbjct   430  CTGTGGGAAAATGAACTCTCGGGTTTTATGAATCATGATATTTGGGTTCAAGATATTAAT   489

Query   360  GGTGATGGACTTGTAGAGATATTTGCTGCGAATGCCGATGGCAATGTTTACTGTATTAAT   419
             ||||||||||||||||||||||||||||||||||||||||||||||||||||||||||||
Sbjct   490  GGTGATGGACTTGTAGAGATATTTGCTGCGAATGCCGATGGCAATGTTTACTGTATTAAT   549

Query   420  AGTGATGGTTCTTTAAAGTGGACGTTTGGTCTAAATGAAGTCCCTATGAACTCTGTAACT   479
             ||||||||||||||||||||||||||||||||||||||||||||||||||||||||||||
Sbjct   550  AGTGATGGTTCTTTAAAGTGGACGTTTGGTCTAAATGAAGTCCCTATGAACTCTGTAACT   609

Query   480  GTAATCTCTGATGCAGATATAAAGTATGTTGTGGCAGGTGGTTACGATAAAAACTTGTAT   539
             |||||||||||||||||||| |||||||||||||||||||||||||||||||||||||||
Sbjct   610  GTAATCTCTGATGCAGATAAAAAGTATGTTGTGGCAGGTGGTTACGATAAAAACTTGTAT   669

Query   540  TACATATCGACTAATGGAGAACTTTTTAAAACAATTGAATCAGGTACTTACTCAGAAGAA   599
             ||||||||||||||||||| ||||||||| ||||||||||||||||||||||||||||||
Sbjct   670  TACATATCGACTAATGGTGAACTTTTAAAAACAATTGAATCAGGTACTTACTCAGAAGAA   729

Query   600  GGGGTGTTTGG   610
             |||||||||||
Sbjct   730  GGGGTGTTTGG   740
```

[FIG. 3]
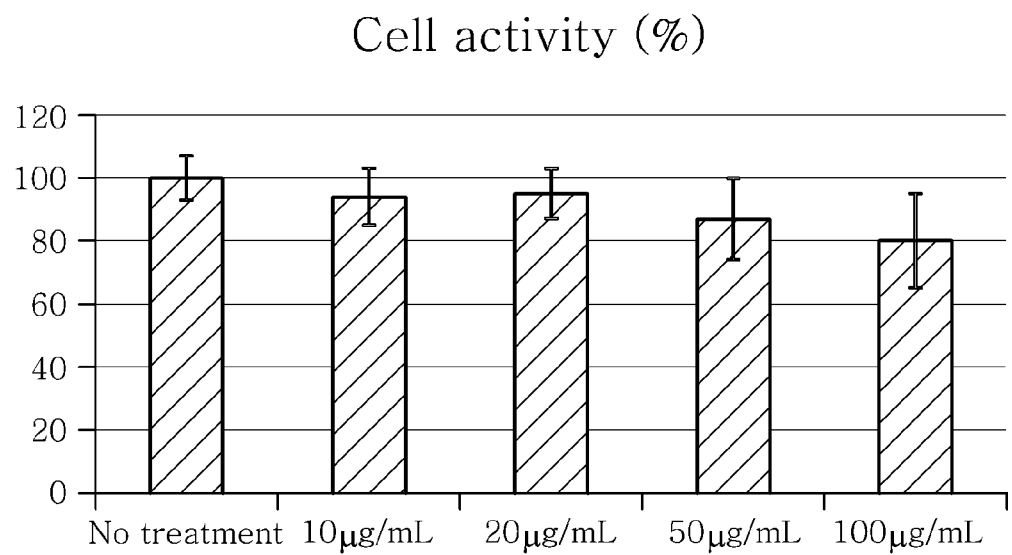
[FIG. 4]
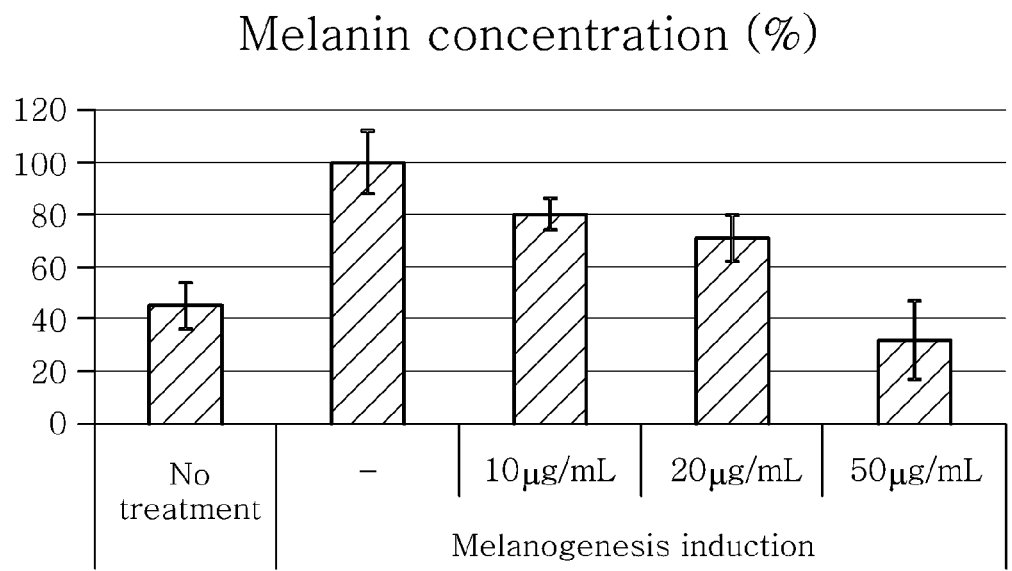

[FIG. 5]
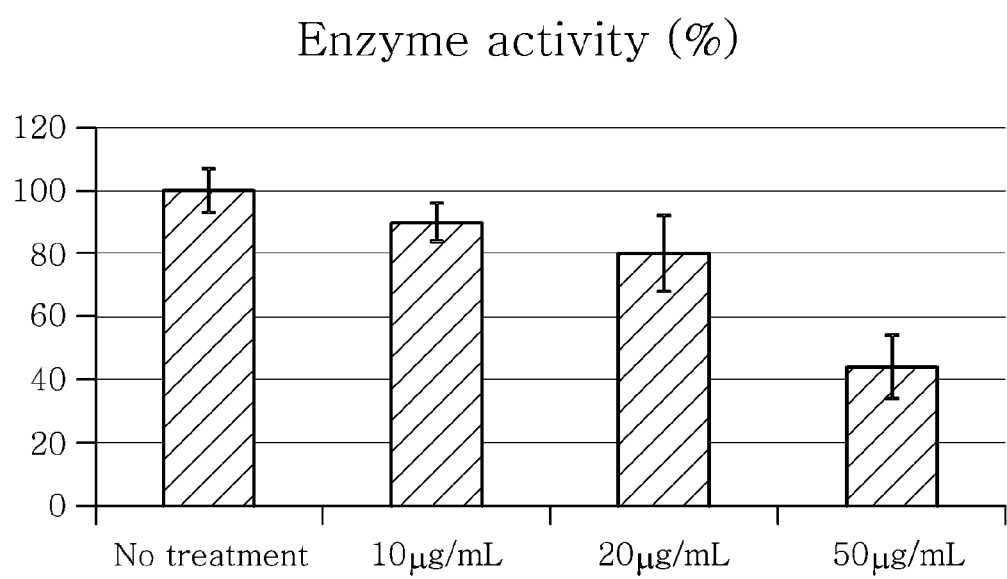

SKIN WHITENING COMPOSITION COMPRISING CULTURE OF PSEUDOALTEROMONAS CARRAGEENOVORA OR EXTRACT THEREOF

CROSS REFERENCE TO RELATED APPLICATIONS

This application is a National Stage of International Application No. PCT/KR2018/011114, filed Sep. 20, 2018, claiming priority to Korean Patent Application No. 10-2017-0125339, filed Sep. 27, 2017.

TECHNICAL FIELD

Disclosed in the present specification is a skin whitening composition containing a *Pseudoalteromonas carrageenovora* strain, a lysate thereof, a cultured product thereof, or an extract of the strain, lysate or cultured product as an active ingredient.

BACKGROUND ART

Human skin color is determined by carotene, the amount of melanin, hemoglobin, etc. Among them, melanin plays the most important role. Melanin is a pigment responsible for skin color and the color of hair and eye and plays an important role of protecting human skin. However, excessive production of melanin in the skin due to external environments such as excessive exposure to UV, air pollution, stress, etc. causes skin darkening, liver spots, freckles, etc. UV radiation is the major factor that induces melanin overproduction through promotion of the activity of melanin-producing melanocytes, promotion of the secretion of melanin biosynthesis-stimulating hormones, promotion of melanin oxidation, promotion of tyrosinase activity, etc. The most recognizable feature of the melanin production mechanism is that the enzyme called tyrosinase is involved. Therefore, skin whitening effect may be expected if the melanin production is prevented by inhibiting the activity of tyrosinase.

A *Pseudoalteromonas carrageenovora* strain is a one of marine bacteria known to form biofilms. Although many researches have been conducted on carrageenan, which is an extracellular polysaccharide (EPS), nothing is known about the use of the strain itself.

REFERENCES OF RELATED ART

Patent Documents

Korean Patent Registration Publication No. 10-0812922.

DISCLOSURE

Technical Problem

In an aspect, the present specification is directed to providing a new use of a *Pseudoalteromonas carrageenovora* strain.

In another aspect, the present specification is directed to providing a *Pseudoalteromonas carrageenovora* SNC 121 strain having superior skin whitening activity.

Technical Solution

In another aspect, the present specification provides a skin whitening composition containing: a *Pseudoalteromonas carrageenovora* strain; a lysate thereof; a cultured product thereof; or an extract of the strain, lysate or cultured product as an active ingredient.

In an exemplary embodiment, the strain may be *Pseudoalteromonas carrageenovora* SNC 121 having an accession number of KCCM12049P.

In an exemplary embodiment, the strain may have 16S rDNA including a base sequence of SEQ ID NO 1.

In an exemplary embodiment, the cultured product may be cultured in a culture medium including one or more selected from a group consisting of starch, yeast extract, peptone and sea salt.

In an exemplary embodiment, the extract may be an ethyl acetate fraction.

In an exemplary embodiment, the active ingredient may be contained in an amount of 0.001-30 wt % based on the total weight of the composition.

In an exemplary embodiment, the composition may inhibit melanin production or tyrosinase activity.

In an exemplary embodiment, the composition may be a cosmetic composition.

In another aspect, the present specification provides a *Pseudoalteromonas carrageenovora* SNC 121 strain having an accession number of KCCM12049P, having skin whitening function.

In an exemplary embodiment, the strain may be isolated from coral.

Advantageous Effects

In an aspect, the present specification provides an environment-friendly skin whitening ingredient.

In another aspect, the present specification provides a use of a *Pseudoalteromonas carrageenovora* strain for skin whitening. The strain has an effect of inhibiting melanin production in melanocytes.

In another aspect, the present specification provides a *Pseudoalteromonas carrageenovora* SNC 121 strain having superior skin whitening activity.

BRIEF DESCRIPTION OF DRAWINGS

FIG. 1 shows the 16s rDNA sequence (SEQ ID NO 1) of a *Pseudoalteromonas carrageenovora* SNC 121 strain having an accession number of KCCM12049P according to the present specification.

FIG. 2 shows a result of comparing a part of the λ-carrageenase sequence of *P. carrageenovora* SNC 121 according to an exemplary embodiment of the present specification with a part of the λ-carrageenase sequence of *P. carrageenovora* NBRC 12985 (ATCC43555T).

FIG. 3 shows the skin cell safety of a *Pseudoalteromonas carrageenovora* strain according to an exemplary embodiment of the present specification.

FIG. 4 shows the melanin production inhibiting effect of a *Pseudoalteromonas carrageenovora* strain according to an exemplary embodiment of the present specification.

FIG. 5 shows the effect of inhibiting the activity of a melanin-producing enzyme of a *Pseudoalteromonas carrageenovora* strain according to an exemplary embodiment of the present specification.

BEST MODE

Hereinafter, the present disclosure is described in detail.

In an aspect, the present specification provides a skin whitening composition containing: a *Pseudoalteromonas*

*carrageenovora* strain; a lysate thereof; a cultured product thereof; or an extract of the strain, lysate or cultured product as an active ingredient.

In another aspect, the present specification provides a method for enhancing skin whitening, which includes administering a *Pseudoalteromonas carrageenovora* strain, a lysate thereof, a cultured product thereof, or an extract of the strain, lysate or cultured product of an amount effective for enhancing skin whitening to a subject in need thereof.

In another aspect, the present specification provides a *Pseudoalteromonas carrageenovora* strain, a lysate thereof, a cultured product thereof, or an extract of the strain, lysate or cultured product for enhancing skin whitening of a subject.

In another aspect, the present specification provides a non-therapeutic use of a *Pseudoalteromonas carrageenovora* strain, a lysate thereof, a cultured product thereof, or an extract of the strain, lysate or cultured product for enhancing skin whitening of a subject.

In another aspect, the present specification provides a use of a *Pseudoalteromonas carrageenovora* strain, a lysate thereof, a cultured product thereof, or an extract of the strain, lysate or cultured product for preparing a composition for enhancing skin whitening.

In another aspect, the present specification provides a *Pseudoalteromonas carrageenovora* SNC 121 strain having an accession number of KCCM12049P.

In an exemplary embodiment, the *Pseudoalteromonas carrageenovora* strain, the lysate thereof, the cultured product thereof, or the extract of the strain, lysate or cultured product may be administered or applied or spreaded to a subject in the form of a composition, e.g., a composition for external application to skin or a cosmetic composition.

In an exemplary embodiment, the *Pseudoalteromonas carrageenovora* strain, the lysate thereof, the cultured product thereof, or the extract of the strain, lysate or cultured product may be administered to the skin of a subject.

In an exemplary embodiment, the strain may be preferred to be *Pseudoalteromonas carrageenovora* SNC 121 having an accession number of KCCM12049P.

In an exemplary embodiment, the strain may have 16S rDNA including the base sequence of SEQ ID NO 1.

In an exemplary embodiment, the *Pseudoalteromonas carrageenovora* SNC 121 strain may have skin whitening function.

In the present specification, the "active ingredient" refers to an ingredient capable of affording a desired activity either alone or together with a carrier, etc. which has no activity in itself.

Microbial resources are advantageous in that they can be utilized as renewable resources unlike petroleum, water, etc.

In an exemplary embodiment, the strain may be prepared as follows. After culturing the strain and centrifuging the culture medium, followed by washing with sterilized physiological saline and suspending in a solvent, e.g., sterilized milk, it may be prepared into freeze-dried powder.

The lysate of the strain may refer to a product obtained by lysing the strain itself either chemically or by applying physical force.

The cultured product of the strain may refer to a material comprising some or all substances included in the culture medium in which the strain was cultured, regardless of the type of the cultured product. For example, it may refer to a substance including a metabolite or a secreted product resulting from the culturing of the strain, or a lysate thereof, and the strain itself may also be included in the cultured product.

In an exemplary embodiment, the cultured product may be cultured in a culture medium including one or more selected from a group consisting of starch, yeast extract, peptone and sea salt.

The extract may refer to a product obtained by extracting, isolating or fractionating the strain itself, a lysate of the strain, a cultured product of the strain or a mixture thereof, regardless of extraction method, extraction solvent, extracted ingredients or type of the extract. The term is used in a broad concept, including any substance that can be obtained through processing or treating after the extraction.

In an exemplary embodiment, the extract may be an ethyl acetate fraction of a culture of *Pseudoalteromonas carrageenovora*.

In an exemplary embodiment, the *Pseudoalteromonas carrageenovora* strain, the lysate thereof, the cultured product thereof, or the extract of the strain, lysate or cultured product may be contained in an amount of 0.001-30 wt % based on the total weight of the composition. In another aspect, the *Pseudoalteromonas carrageenovora* strain, the lysate thereof, the cultured product thereof, or the extract of the strain, lysate or cultured product may be contained in an amount of 0.001 wt % or more, 0.01 wt % or more, 0.1 wt % or more, 0.5 wt % or more, 1 wt % or more, 1.5 wt % or more or 2 wt % or more, and 30 wt % or less, 25 wt % or less, 20 wt % or less, 15 wt % or less, 10 wt % or less or 5 wt % or less, based on the total weight of the composition.

The *Pseudoalteromonas carrageenovora* strain, the lysate thereof, the cultured product thereof, the extract of the strain, lysate or cultured product, or the skin whitening composition containing the same according to the present disclosure has an effect of preventing, improving and/or treating a symptom or a disease caused by melanin overproduction by effectively inhibiting melanin production.

In an exemplary embodiment, the symptom or disease caused by melanin overproduction may be one or more selected from a group consisting of liver spots, freckles, age spots, blemish, epidermal melanocytic lesions, café au lait macules, Beckers nevus, nevus spilus, lentigines, dermal melanocytic lesions, Mongolian spot, nevus of Ota, acquired bilateral nevus of Ota-like macules, nevus of Ito, blue nevus, melanocytic nevus, junctional nevus, compound nevus, intradermal nevus, halo nevus, congenital nevocytic nevus, Spitz nevus, dysplastic nevus, melanoma, lentigo maligna melanoma, superficial spreading melanoma, acral lentiginous melanoma, nodular melanoma, pigmented basal cell carcinoma, pigmented dermatofibromas, dermoid cyst, pigmented keloid and pigmented keratoacanthomas.

In an exemplary embodiment, the *Pseudoalteromonas carrageenovora* strain, the lysate thereof, the cultured product thereof, the extract of the strain, lysate or cultured product, or the composition containing the same may prevent, improve and/or treat skin pigmentation.

In an exemplary embodiment, the *Pseudoalteromonas carrageenovora* strain, the lysate thereof, the cultured product thereof, the extract of the strain, lysate or cultured product, or the composition containing the same may prevent, improve and/or treat one or more skin pigmentation selected from a group consisting of liver spots, freckles, dark spots, nevus, melanoma, drug-induced pigmentation, inflammation-induced pigmentation and dermatitis-induced pigmentation, which occurs topically in skin due to increased melanin production.

In an exemplary embodiment, the composition may be a composition for external application to skin.

In an exemplary embodiment, the composition for external application to skin may further contain a pharmaceutical adjuvant such as antiseptic, a stabilizer, a wetting agent, an emulsification promoter, a salt and/or a buffer for controlling osmotic pressure, etc. and other therapeutically useful substances in addition to the active ingredient according to the present specification, and may be formulated into various forms for parenteral application according to common methods.

In an exemplary embodiment, the formulation for parenteral application may be for transdermal application. For example, the formulation may be an injection, an ointment, a lotion, a gel, a cream, a spray, a suspension, an emulsion, a patch, etc., although not being limited thereto.

In an exemplary embodiment, the composition for external application to skin may be a topical medication having pharmaceutical use for a disease related with melanin production.

In an exemplary embodiment, the composition may be a cosmetic composition.

In an exemplary embodiment, the cosmetic composition may further contain functional additives and ingredients contained in general cosmetic compositions in addition to the active ingredient according to the present specification. The functional additive may be an ingredient selected from a group consisting of a water-soluble vitamin, an oil-soluble vitamin, a polypeptide, a polysaccharide, a sphingolipid and a seaweed extract. In addition, an ingredient such as an oil, a fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a fragrance, a blood circulation stimulant, a cooling agent, an antiperspirant, purified water, etc. may be further contained.

The formulation of the cosmetic composition is not particularly limited and may be selected adequately depending on purposes. For example, the cosmetic composition may be prepared into one or more formulation selected from a group consisting of a skin lotion, a skin softener, a skin toner, an astringent, a lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion and a body cleanser, although not being limited thereto.

In an exemplary embodiment, when the formulation of the present disclosure is a paste, a cream or a gel, an animal fiber, a plant fiber, a wax, paraffin, starch, tragacanth, a cellulose derivative, polyethylene glycol, silicone, bentonite, silica, talc, zinc oxide, etc. may be used as a carrier ingredient.

In an exemplary embodiment, when the formulation of the present disclosure is a powder or a spray, lactose, talc, silica, aluminum hydroxide, calcium silicate or polyamide powder may be used as a carrier ingredient. In particular, when the formulation is a spray, it may further contain a propellant such as chlorofluorohydrocarbon, propane/butane or dimethyl ether.

In an exemplary embodiment, when the formulation of the present disclosure is a solution or an emulsion, a solvent, a solubilizer or an emulsifier, e.g., water, ethanol, isopropanol, ethyl carbonate, ethyl acetate, benzyl alcohol, benzyl benzoate, propylene glycol, 1,3-butylene glycol, a glycerol aliphatic ester, polyethylene glycol or a fatty acid ester of sorbitan may be used as a carrier ingredient.

In an exemplary embodiment, when the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

In an exemplary embodiment, when the formulation of the present disclosure is a surfactant-containing cleanser, an aliphatic alcohol sulfate, an aliphatic alcohol ether sulfate, sulfosuccinic monoester, isethionate, an imidazolinium derivative, methyl taurate, sarcosinate, a fatty acid amide ether sulfate, an amidoalkyl betaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

Mode for Invention

Hereinafter, the present disclosure will be described in detail through examples. However, the following examples are for illustrative purposes only and it will be apparent to those of ordinary skill in the art that the scope of the present disclosure is not limited by the examples.

Example 1. Isolation and Identification of Strain

Coral harvested near in the sea near Jeju Island was heat-treated at 60° C. for 10 minutes to remove Gram-negative bacteria on the coral surface. Then, microorganisms existing on the coral surface were isolated using physiological saline (0.85% NaCl). The physiological saline solution was diluted 10-fold and 100-fold using physiological saline and then inoculated to an isolation medium (10 g/L starch, 4 g/L yeast extract, 2 g/L peptone, 16 g/L agar, 34.75 g/L sea salt) supplemented with an antibiotic (chloramphenicol 20 μg/mL). The inoculated medium was incubated at 27° C. for 7-30 days, and a single strain forming a colony was isolated finally by subculturing for 2-4 passages.

The isolated strain was identified through 16S rRNA base sequencing using 27F (5'-AGAGTTT-GATCMTGGCTCAG-3', SEQ ID NO 2) and 1492R (5'-TACGGYTACCTTGTTACGACTT-3', SEQ ID NO 3) primers. As a result of Gene Bank search, the isolated strain was confirmed to have 100% similarity to *Pseudoalteromonas carrageenovora* strain NBRC 12985 and named as *Pseudoalteromonas carrageenovora* SNC 121. The strain was deposited on Jun. 27, 2017 in the Korean Culture Center of Microorganisms (KCCM) and was given the accession number KCCM12049P.

As a result of comparing a part of the A-carrageenase sequence of *P. carrageenovora* SNC 121 with a part of the A-carrageenase sequence of *P. carrageenovora* NBRC 12985 (ATCC43555T), the two strains were identified as different strains exhibiting 99% similarity (see FIG. 2).

Example 2. Preparation of Cultured Product and Extract of *Pseudoalteromonas carrageenovora* Strain The *Pseudoalteromonas carrageenovora* SNC 121 strain identified in Example 1 was inoculated to a culture medium (10 g/L starch, 2 g/L yeast extract, 4 g/L peptone, 34.75 g/L sea salt) and a culture of the *Pseudoalteromonas carrageenovora* strain was obtained by culturing the same at 27° C. and 120 rpm for 7 days.

The obtained culture of the *Pseudoalteromonas carrageenovora* strain was added to ethyl acetate of the same volume and an ethyl acetate fraction was obtained by conducting reaction. The ethyl acetate fraction did not contain the carrageenan which is an exopolysaccharide (EPS) of the culture, sugars, proteins, etc. Then, an extract was obtained by removing the ethyl acetate using an evaporator.

Example 3. Confirmation of Skin Cell Safety of *Pseudoalteromonas carrageenovora* Strain Experiment was conducted as follows to investigate whether the *Pseudoalteromonas carrageenovora* strain is safe for skin cells.

Specifically, after dissolving the extract of the *Pseudoalteromonas carrageenovora* strain isolated from the coral obtained in Example 2 in DMSO (dimethyl sulfoxide) and treating skin cells (HaCaT) with the extract, the effect on the activity of the cells was investigated. After seeding 100 μL of the skin cells onto a 96-well cell culture plate at a concentration of $2 \times 10^5$ cells/mL and culturing for 24 hours, followed by treating with the extract of the *Pseudoalteromonas carrageenovora* strain at concentrations of 10-100 μg/mL, the cells were cultured further for 24 hours. The experiment was repeated 3 times for the respective concentrations. The cell activity was compared by MTT assay and was represented relative to the activity of the untreated group as 100%.

As a result, the *Pseudoalteromonas carrageenovora* strain isolated from the coral was confirmed to be safe the skin cells since they had no effect on the growth of the skin cells (see FIG. 3).

Example 4. Confirmation of Skin Whitening Effect of *Pseudoalteromonas carrageenovora* Strain The skin whitening effect of the *Pseudoalteromonas carrageenovora* strain was tested as follows.

Specifically, the skin whitening effect was evaluated by treating melanocytes (B16 melanoma cells) with the extract of the *Pseudoalteromonas carrageenovora* strain isolated from the coral obtained in Example 2. The melanocytes seeded onto a 24-well cell culture plate at a concentration of $4 \times 10^4$ cells/well and cultured for 24 hours were used for the experiment. The cells were treated with 1 μM α-MSH (α-melanocyte-stimulating hormone) to induce melanin production and at the same time with the extract of the *Pseudoalteromonas carrageenovora* strain at concentrations of 10-50 μg/mL. The experiment was repeated 3 times for the respective concentrations. After culturing further for 72 hours, absorbance was measured at 405 nm in order to compare the melanin content in the culture medium. The degree of melanin production of the groups treated with the extract was represented relative to the absorbance of the melanin production-induced group as 100%.

In addition, tyrosinase activity was compared by reacting mushroom tyrosinase with the extract for a predetermined time using L-tyrosine as a substrate and then measuring absorbance at 475 nm. After adding tyrosinase to a buffer (0.1 M potassium phosphate buffer) at a concentration of 2 units/μL, the substrate concentration was adjusted to 0.3 mg/mL. Then, after adding the extract at concentrations of 10-50 μg/mL and 100 μL of L-DOPA, absorbance was measured immediately at 475 nm. Then, after conducting reaction at 37° C. for 10 minutes, absorbance was measured again. The difference in the absorbance of the extract-treated groups was represented relative to the difference in the absorbance of the untreated group as 100%.

As a result, it was confirmed that the extract inhibited the melanin production in the melanocytes in a concentration-dependent manner (see FIG. 4), which was due to the inhibited activity of the melanin-producing enzyme tyrosinase (see FIG. 5). Accordingly, it was confirmed that the *Pseudoalteromonas carrageenovora* strain has skin whitening effect.

Hereinafter, formulation examples of the composition according to an aspect of the present disclosure will be described. However, the following formulation examples are for illustrative purposes only and the scope of the present disclosure is not limited by them.

Formulation Example 1. Softening Lotion

A softening lotion was prepared according to a common method by mixing 0.01 wt % of the *Pseudoalteromonas carrageenovora* culture of Example 2, 3 wt % of glycerin, 2 wt % of butylene glycol, 2 wt % of propylene glycol, 0.1 wt % of a carboxyvinyl polymer, 10 wt % of ethanol, 0.1 wt % of triethanolamine, an antiseptic as balance, a trace amount of a colorant, a trace amount of a fragrance and a trace amount of purified water.

Formulation Example 2. Nourishing Lotion

A nourishing lotion was prepared according to a common method by mixing 0.01 wt % of the *Pseudoalteromonas carrageenovora* culture of Example 2, 4 wt % of beeswax, 1.5 wt % of polysorbate 60, 0.5 wt % of sorbitan sesquioleate, 5 wt % of liquid paraffin, 5 wt % of squalane, 5 wt % of caprylic/capric triglyceride, 3 wt % of glycerin, 3 wt % of butylene glycol, 3 wt % of propylene glycol, 0.1 wt % of a carboxyvinyl polymer, 0.2 wt % of triethanolamine, an antiseptic as balance, a trace amount of a colorant, a trace amount of a fragrance and a trace amount of purified water.

Formulation Example 3. Nourishing Cream

A nourishing cream was prepared according to a common method by mixing 0.01 wt % of the *Pseudoalteromonas carrageenovora* culture of Example 2, 10 wt % of beeswax, 1.5 wt % of polysorbate 60, 0.5 wt % of sorbitan sesquioleate, 10 wt % of liquid paraffin, 5 wt % of squalane, 5 wt % of caprylic/capric triglyceride, 5 wt % of glycerin, 3 wt % of butylene glycol, 3 wt % of propylene glycol, 0.2 wt % of triethanolamine, an antiseptic as balance, a trace amount of a colorant, a trace amount of fragrance and a trace amount of purified water.

Formulation Example 4. Pack

A pack was prepared according to a common method by mixing 0.01 wt % of the *Pseudoalteromonas carrageenovora* culture of Example 2, 13 wt % of polyvinyl alcohol, 0.2 wt % of sodium carboxymethyl cellulose, 0.1 wt % of allantoin, 5 wt % of ethanol, 0.3 wt % of nonyl phenyl ether, an antiseptic as balance, a trace amount of a colorant, a trace amount of fragrance and a trace amount of purified water.

Although the particular embodiments of the present disclosure have been described in detail, it will be apparent to those of ordinary skill in the art that they are only specific exemplary embodiments and the scope of the present disclosure is not limited by them. Accordingly, the substantial scope of the present disclosure will be defined by the appended claims and their equivalents.

ACCESSION NUMBER

Depository authority: Korean Culture Center of Microorganisms
   Accession number: KCCM12049P
   Date of deposition: Jun. 27, 2017

---

The invention claimed is:

1. A method for enhancing skin whitening, which comprises administering a *Pseudoalteromonas carrageenovora* strain; a lysate thereof; a cultured product thereof; or an extract of the strain, lysate or cultured product of an amount effective for enhancing skin whitening to a subject in need thereof.

2. The method for enhancing skin whitening according to claim 1, wherein the strain is *Pseudoalteromonas carrageenovora* SNC 121 having accession number of KCCM12049P.

3. The method for enhancing skin whitening according to claim 2, wherein the strain has 16S rDNA comprising the base sequence of SEQ ID NO 1.

4. The method for enhancing skin whitening according to claim 1, wherein the cultured product is cultured in a culture medium comprising one or more selected from the group consisting of starch, yeast extract, peptone and sea salt.

5. The method for enhancing skin whitening according to claim 1, wherein the extract is an ethyl acetate fraction.

6. The method for enhancing skin whitening according to claim 1, wherein the *Pseudoalteromonas carrageenovora* strain, the lysate thereof, the cultured product thereof, or the extract of the strain, lysate or cultured product is administered in the form of a composition, and the *Pseudoalteromonas carrageenovora* strain, the lysate thereof, the cultured product thereof, or the extract of the strain, lysate or cultured product is comprised in an amount of 0.001-30 wt % based on the total weight of the composition.

7. The method for enhancing skin whitening according to claim 6, wherein the composition inhibits the activity of a melanin-producing enzyme.

8. The method for enhancing skin whitening according to claim 6, wherein the composition is a cosmetic composition.

\* \* \* \* \*

SEQUENCE LISTING

<160> NUMBER OF SEQ ID NOS: 3

<210> SEQ ID NO 1
<211> LENGTH: 1391
<212> TYPE: DNA
<213> ORGANISM: Unknown
<220> FEATURE:
<223> OTHER INFORMATION: Pseudoalteromonas carrageenovora SNC121

<400> SEQUENCE: 1

```
agcggtaaca gaaagtagct tgctactttg ctgacgagcg gcggacgggt gagtaatgct      60
tgggaacatg ccttgaggtg ggggacaaca gttggaaacg actgctaata ccgcataatg     120
tctacggacc aaagggggct tcggctctcg cctttagatt ggcccaagtg ggattagcta     180
gttggtgagg taatggctca ccaaggcaac gatccctagc tggtttgaga ggatgatcag     240
ccacactgga actgagacac ggtccagact cctacgggag gcagcagtgg ggaatattgc     300
acaatgggcg caagcctgat gcagccatgc cgcgtgtgtg aagaaggcct tcgggttgta     360
aagcactttc agtcaggagg aaaggttagt agttaatacc tgctagctgt gacgttactg     420
acagaagaag caccggctaa ctccgtgcca gcagccgcgg taatacgag ggtgcgagcg     480
ttaatcggaa ttactgggcg taaagcgtac gcaggcggtt tgttaagcga gatgtgaaag     540
ccccgggctc aacctgggaa ctgcatttcg aactggcaaa ctagagtgtg atagagggtg     600
gtagaatttc aggtgtagcg gtgaaatgcg tagagatctg aaggaatacc gatggcgaag     660
gcagccacct gggtcaacac tgacgctcat gtacgaaagc gtggggagca acaggatta     720
gataccctgg tagtccacgc cgtaaacgat gtctactaga agctcggaac ctcggttctg     780
tttttcaaag ctaacgcatt aagtagaccg cctggggagt acggccgcaa ggttaaaact     840
caaatgaatt gacgggggcc cgcacaagcg gtggagcatg tggtttaatt cgatgcaacg     900
cgaagaacct tacctacact tgacatacag agaacttacc agagatggtt tggtgccttc     960
gggaactctg atacaggtgc tgcatggctg tcgtcagctc gtgttgtgag atgttgggtt    1020
aagtcccgca acgagcgcaa ccctatcct tagttgctag caggtaatgc tgagaactct    1080
aaggagactg ccggtgataa accggaggaa ggtggggacg acgtcaagtc atcatggccc    1140
ttacgtgtag gctacacac gtgctacaat ggcgcataca gagtgctgcg aactcgcgag    1200
agtaagcgaa tcacttaaag tgcgtcgtag tccggattgg agtctgcaac tcgactccat    1260
gaagtcggaa tcgctagtaa tcgcgtatca gaatgacgcg gtgaatacgt tcccgggcct    1320
tgtacacacc gcccgtcaca ccatgggagt gggttgctcc agaagtagat agtctaaccc    1380
tcgggaggac g                                                         1391
```

<210> SEQ ID NO 2
<211> LENGTH: 20
<212> TYPE: DNA
<213> ORGANISM: Artificial Sequence
<220> FEATURE:
<223> OTHER INFORMATION: 27F primer

<400> SEQUENCE: 2

```
agagtttgat cmtggctcag                                                   20
```

```
<210> SEQ ID NO 3
<211> LENGTH: 22
<212> TYPE: DNA
<213> ORGANISM: Artificial Sequence
<220> FEATURE:
<223> OTHER INFORMATION: 1492R primer

<400> SEQUENCE: 3
tacggytacc ttgttacgac tt                                               22
```